US012697010B2

(12) United States Patent
Kok et al.

(10) Patent No.: US 12,697,010 B2
(45) Date of Patent: Aug. 4, 2026

(54) IMAGE ENHANCEMENT OF ANATOMICAL FEATURES

(71) Applicant: Leica Instruments (Singapore) Pte. Ltd., Singapore (SG)

(72) Inventors: Alvin Kok, Singapore (SG); Gao Yang, Singapore (SG); Zheng-Dong Zeng, Singapore (SG); Jiahao Pan, Singapore (SG)

(73) Assignee: Leica Instruments (Singapore) Pte Ltd., Singapore (SG)

( * ) Notice: Subject to any disclaimer, the term of this patent is extended or adjusted under 35 U.S.C. 154(b) by 298 days.

(21) Appl. No.: 18/552,922

(22) PCT Filed: Mar. 31, 2022

(86) PCT No.: PCT/EP2022/058675
§ 371 (c)(1),
(2) Date: Sep. 28, 2023

(87) PCT Pub. No.: WO2022/207851
PCT Pub. Date: Oct. 6, 2022

(65) Prior Publication Data
US 2024/0188796 A1 Jun. 13, 2024

(30) Foreign Application Priority Data
Mar. 31, 2021 (EP) .................................... 21166432

(51) Int. Cl.
A61B 1/00 (2006.01)
A61B 34/00 (2016.01)
A61B 90/00 (2016.01)

(52) U.S. Cl.
CPC .... A61B 1/000095 (2022.02); A61B 1/00006 (2013.01); A61B 1/0004 (2022.02);
(Continued)

(58) Field of Classification Search
CPC .......... A61B 1/000095; A61B 1/00006; A61B 1/0004; A61B 34/25; A61B 34/2554;
(Continued)

(56) References Cited

U.S. PATENT DOCUMENTS

| 10,335,572 B1 * | 7/2019 | Kumar | .................... G06F 3/015 |
| 11,723,805 B2 * | 8/2023 | Berlin | ................. A61F 9/00802 |
| | | | 606/4 |

(Continued)

FOREIGN PATENT DOCUMENTS

| EP | 3263013 A1 | 1/2018 |
| JP | 2015230703 A | 12/2015 |

(Continued)

*Primary Examiner* — Andrew W Bee

(74) *Attorney, Agent, or Firm* — 2SPL Patent Attorneys PartG mbB; Yong Beom Hwang

(57) ABSTRACT

An apparatus for processing image data of tissue that includes at least one processor is disclosed. The apparatus is configured for determining a profile from a plurality of profiles, and applying a plurality of settings from the determined profile. The apparatus determines the image based on the applied settings, and outputs data for displaying at least one image. Each profile includes a plurality of settings. Each profile can be configured to enhance and/or suppress anatomical features of the image.

15 Claims, 8 Drawing Sheets

(52) U.S. Cl.
CPC .............. *A61B 34/25* (2016.02); *A61B 90/36*
(2016.02); *A61B 90/37* (2016.02)

(58) Field of Classification Search
CPC .................... A61B 90/36; A61B 90/37; G06T
2207/30004; G06T 2207/30041
See application file for complete search history.

(56) References Cited

U.S. PATENT DOCUMENTS

| | | | |
|---|---|---|---|
| 2007/0078678 A1* | 4/2007 | DiSilvestro | ............ A61B 34/20 |
| | | | 600/407 |
| 2009/0089081 A1* | 4/2009 | Haddad | .................. G16H 50/50 |
| | | | 705/2 |
| 2012/0130258 A1 | 5/2012 | Taylor et al. | |
| 2012/0184846 A1 | 7/2012 | Izatt et al. | |
| 2014/0235945 A1 | 8/2014 | Mcdowall | |
| 2016/0183779 A1 | 6/2016 | Ren et al. | |
| 2016/0278678 A1 | 9/2016 | Valdes et al. | |
| 2021/0382559 A1* | 12/2021 | Segev | .................. G06V 10/806 |

FOREIGN PATENT DOCUMENTS

| | | | |
|---|---|---|---|
| JP | 2019162336 A | 9/2019 | |
| JP | 2020058800 A | 4/2020 | |
| WO | 20200084625 A1 | 4/2020 | |

* cited by examiner

IMAGE ENHANCEMENT OF ANATOMICAL FEATURES

TECHNICAL FIELD

Examples disclosed herein relate to surgical apparatuses such as microscopes and image processing particularly of live tissue.

BACKGROUND

Modern surgical apparatuses may be utilized for a range of procedures. Each procedure may allow a user to adjust apparatus settings to the procedure. For example, surgical microscopes may allow users to visualize different anatomical features. Surgical apparatuses such as microscopes may be used for a wide range of procedures and may have adaptable settings to accommodate different procedures. It can be challenging to improve user experiences with medical apparatuses, such as surgical microscopes, for example due to the diversity of procedures and range of device settings which may be possible.

SUMMARY

It may be desirable to adjust visual images of tissue to allow optimal visualization of certain features, or suppress other features, in order to provide a user such as a medical professional or surgeon with optimally relevant content for analysis or surgical intervention. Reproducible and/or handy settings adjustments can reduce uncertainty and error in treatment and analysis of tissue, particularly in a surgical setting and/or when live tissue is involved. Reproducible and/or handy settings adjustments for apparatuses used for imaging are desirable. Precise and reproducible control of settings that determine the appearance of images of live tissue may aid medical practitioners in the analysis and treatment of disease.

Apparatuses, surgical microscopes, and methods of controlling a display are disclosed herein to address such problems.

Herein is disclosed an apparatus for determining image data of tissue as defined in claim 1. Herein is disclosed a surgical device as defined in claim 14. Herein is disclosed a method of determining an image as defined in claim 15.

In an embodiment, an apparatus for determining image data of tissue includes at least one processor. The apparatus is configured for determining a profile from a plurality of profiles, and applying a plurality of settings from the determined profile. The apparatus determines the image based on the applied settings, and outputs data for displaying at least one image. Each profile includes a plurality of settings. Each profile may be configured to enhance and/or suppress anatomical features of the image. The apparatus may improve image analysis by improving the reproducibility of optimal image settings. A user such as a medical professional may be provided with improved tissue images for analysis or surgical intervention. The determined profile can be selectable from the plurality of profiles. The settings of the determined profile can be adapted to enhance or suppress anatomical features of the at least one image.

In an embodiment, the apparatus is configured such that determining the profile includes: determining a procedure profile from the plurality of profiles, and determining a scene profile from the determined procedure profile. The applied settings are selected from the determined scene profile. The apparatus may improve image analysis and/or tissue treatment by improving the reproducibility of optimal image settings. A user such as a medical professional may be provided with improved tissue images for analysis or surgical intervention.

In an embodiment, the apparatus further comprises at least one memory configured for storing the plurality of profiles and the plurality of settings. The memory can allow a user such as a medical professional to access reproducible settings for improved tissue images for analysis or surgical intervention.

In an embodiment, the apparatus is configured for determining a sequence of sequential scene profiles from the determined procedure profile. Reproducible and/or handy settings adjustments for apparatuses used for imaging can be useful for more efficient image analysis and treatment of disease.

In an embodiment, the apparatus is configured such that applying the plurality of settings includes sequentially applying the sequential scene profiles. Reproducible and/or handy settings adjustments for apparatuses used for imaging can be useful for more efficient image analysis and treatment of disease. The sequence of sequential scene profiles can include at least three scene profiles, each subordinate to the determined procedure profile. For example, the sequential application of scene profiles is such that, after the first settings of the first scene profile are applied, the second settings of the second scene profile are applied. Alternatively/additionally, after the Nth scene profile is applied of a sequence of M scene profiles (M>N), the subsequent N+1 scene profile is applied (until N=M).

In an embodiment, the apparatus is configured such that outputting data includes sequentially outputting a plurality of sequential images at the respective pluralities of applied settings of each sequential scene profile. Reproducible and/or handy settings adjustments for apparatuses used for imaging can be useful for more efficient image analysis and treatment of disease. Precise and reproducible control of settings that determine the appearance of images of live tissue may aid medical practitioners in the analysis and treatment of disease.

In an embodiment, the apparatus is configured for applying the settings of a subsequent scene profile of the determined sequence of scene profiles. Reproducible and/or handy settings adjustments for apparatuses used for imaging can be useful for more efficient image analysis and treatment of disease. Precise and reproducible control of settings that determine the appearance of images of live tissue may aid medical practitioners in the analysis and treatment of disease.

In an embodiment, the apparatus the apparatus is configured for receiving an advance command, and, when the advance command is received, applying the settings of the subsequent scene profile. Reproducible and/or handy settings adjustments for apparatuses used for imaging can be useful for more efficient image analysis and treatment of disease. Precise and reproducible control of settings that determine the appearance of images of live tissue may aid medical practitioners in the analysis and treatment of disease.

In an embodiment, the apparatus further comprising a switch for transmitting the advance command for advancing to the settings of the subsequent scene profile. A switch may aid in simplifying the change of settings.

In an embodiment, the apparatus is configured such that applying the settings (e.g. applying the plurality of settings from the determined profile) includes at least one of processing the image data, or transmitting a control signal to adjust an optical setting. Reproducible and/or handy settings adjustments for apparatuses used for imaging can be useful for more efficient image analysis and treatment of disease. Precise and reproducible control of settings that determine the appearance of images of live tissue may aid medical practitioners in the analysis and treatment of disease. Settings of an applied profile can be adapted to enhance or suppress anatomical features of an image.

In an embodiment, the apparatus is configured such that the plurality of scene profiles includes at least one of the following:

an epiretinal membrane enhancement profile comprising blue or green enhancement for enhancing the epiretinal membrane during peeling;

a vitreous scene profile comprising a blue filter or contrast adjustment for the visualisation of vitreous;

an anterior scene profile in which red reflection is enhanced and an aperture is reduced to increased the depth of field;

a reduced light profile comprising an increased camera exposure time and noise reduction for improving low illumination visualization in the posterior of the eye;

a red enhancement profile comprising an increase in gain of a red channel, for highlighting the posterior capsule for lowering the risk of posterior capsule rupture;

a red-free filter profile for identifying an area for placing a port during hemorrhage;

a red-free filter profile for identifying the retina;

an orange-reddish enhancement profile for aiding differentiation of cornea layers during stripping of a cornea endothelial or descemet's membrane;

a dense cataract profile for adjustment of contrast and enhancing blue or green dye used during rhexis and phacoemulsification of dense cataract lens;

at least one temperature profile for at least one of: a cooler setting, a warmer setting, a 3000 K setting, 4000 K setting, 5000 K setting, a halogen lamp appearance, a fluorescent light appearance, or white LED appearance;

a dye enhancement profile for enhancing contrast from dyes such as indocyanine green, fluorescein, or trypan blue.

The above scene profiles may be particularly useful for enhancing and/or suppressing anatomical features and/or may be often adjusted by medical practitioners. It makes work more efficient to have such profiles available at hand.

In an embodiment, the apparatus is configured such that the plurality of procedure profiles includes at least one of the following:

a cataract procedure profile, comprising at least one or two of: a temperature profile, a red enhancement profile, or a vitreous scene profile for anterior vitrectomy (e.g. all profiles in the list can be applied in a sequence);

a retinal procedure profile, comprising at least one or two of: a temperature profile, an epiretinal membrane enhancement profile, a vitreous scene profile, a reduced light profile, a red-free filter profile, or a dye enhancement profile (e.g. all profiles in the list can be applied in a sequence);

a corneal procedure profile, comprising at least one or two of: a temperature profile, an orange-reddish enhancement profile for aiding differentiation of cornea layers, or a red enhancement profile (e.g. all profiles in the list can be applied in a sequence); or a macular pucker profile, comprising at least one or two of: a temperature profile, an epiretinal membrane enhancement profile, vitreous scene profile, a reduced light profile, red-free filter profile, or a dye enhancement profile (e.g. all profiles in the list can be applied in a sequence).

The above procedure profiles may be particularly useful for enhancing and/or suppressing anatomical features and/or may be often adjusted by medical practitioners. It makes work more efficient to have such profiles available at hand.

In an embodiment, the apparatus is configured for restoring at least one of the settings to a default setting. A plurality of default settings is stored in the at least one memory.

A surgical microscope, such as an ophthalmic surgical microscope, is described herein, comprising any of the apparatuses as described above.

A method of determining at least one image is disclosed herein, comprising determining a profile from a plurality of profiles, applying a plurality of settings from the determined profile, determining the image based on the applied settings, and outputting data for displaying the at least one image. Each profile includes a plurality of settings. Each profile can be adapted to enhance or suppress anatomical features. Precise and reproducible control of settings that determine the appearance of images of live tissue may aid medical practitioners in the analysis and treatment of disease.

SHORT DESCRIPTION OF THE FIGURES

Some examples of apparatuses and/or methods will be described in the following by way of example, and with reference to the accompanying figures, in which.

DETAILED DESCRIPTION

Various examples will now be described more fully with reference to the accompanying drawings in which some examples are illustrated. In the figures, which are not to be assumed to be to scale, the thicknesses of lines, layers and/or regions may be exaggerated for clarity.

As used herein, the term "and/or" includes any and all combinations of one or more of the associated listed items and may be abbreviated as "/". Herein, a trailing "(s)" indicates one or more; for example profile(s) indicates one or more profiles.

Figure 1:
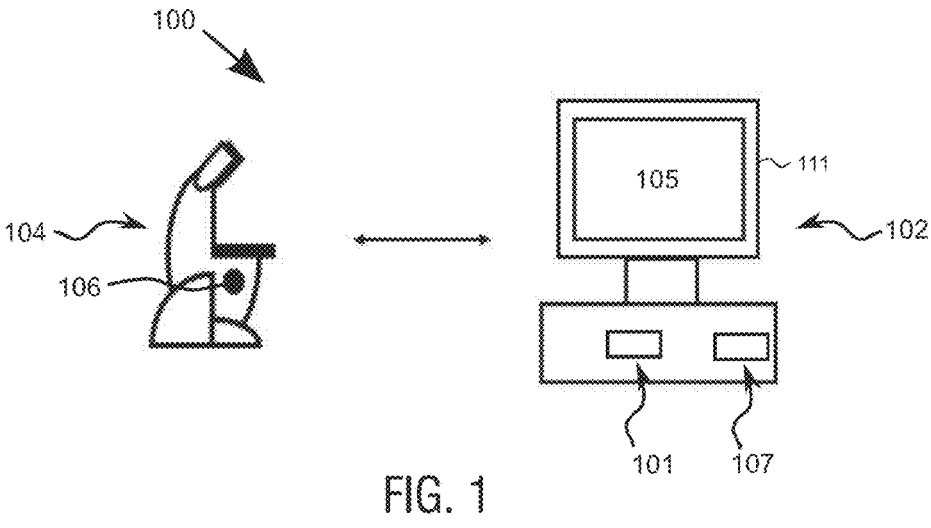
FIG. 1 illustrates a surgical microscope, according to an embodiment described herein.

FIG. 1 illustrates an apparatus 102 for determining image data of tissue. The apparatus 102 has at least one processor 101. The apparatus 102 may be coupled to an imaging device 104, and/or may be part of a surgical microscope 100. The apparatus 102 and/or surgical microscope 100 may include a display 111 for displaying an image(s) 105. The display 111 can be, for example, a 2-D screen, a 3-D screen, or a digital viewer.

The at least one processor 101 can be programmed for determining image data and/or controlling the display 111. For example, the at least one processor 101 can control a display according to the methods illustrated described herein, including the method shown in FIG. 2. The processor(s) 101 can process image data, such as to update or change the image data.

Figure 2:
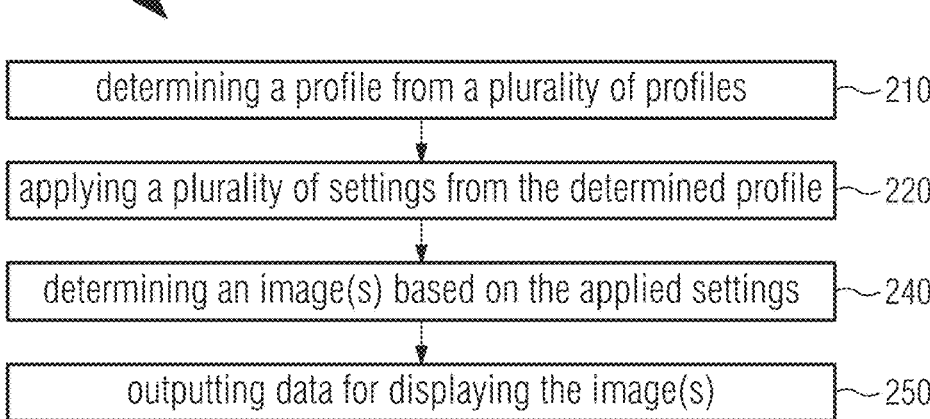
FIG. 2 illustrates a method of determining an image, according to an embodiment described herein.

FIG. 2 illustrates a method 200 of determining image data. The method can include determining 210 a profile 300 from a plurality of profiles 300 (see also FIG. 3). Each profile 300 can include a plurality of settings 400 (see also FIGS. 4A and 4B). Settings 400 can be related to digital settings and/or optical settings which may determine the appearance of images 105. The settings 400 can be stored in the at least one memory 107. The method 200 can include applying 220 a plurality of settings 400 from the determined profile 300, determining 240 the image(s) 105 based on the applied settings 400, and outputting 250 data for displaying at least one image 105. Settings 400 can affect the image(s) 105.

Applying 220 settings 400 can include adjusting brightness, contrast, and noise filtering, to name a few. Settings 400 can include optical adjustments and/or hardware adjustments, such as adjusting the brightness of a light source or the diameter of an aperture. Settings 400 can include digital settings, such as digital filters and noise filters. Each profile 300 can include a plurality of settings 400. Each profile 300 may enhance or suppress anatomical features of the image(s) 105. It is advantageous to be able to reproducibly and/or rapidly adjust settings to enhance or suppress anatomical features. Reproducible and/or rapid application of settings, such as to provide better contrast to features of living tissue of interest, may aid a medical practitioner in analysis and treatment of disease. For example, applying 220 the settings 400 can include processing the image and/or transmitting a control signal to adjust an optical setting.

Processing the image can include applying a digital filter, adjusting the gain of a channel(s) of the image, brightness, contrast, changing average temperature of the image, noise reduction, and combinations thereof. Transmitting a control signal to apply 220 settings can include adjusting an aperture (e.g. adjusting the size of an iris and/or diaphragm), brightness, focus, selecting a light source, changing an optical filter, changing a detector, and combinations thereof.

Figure 3:
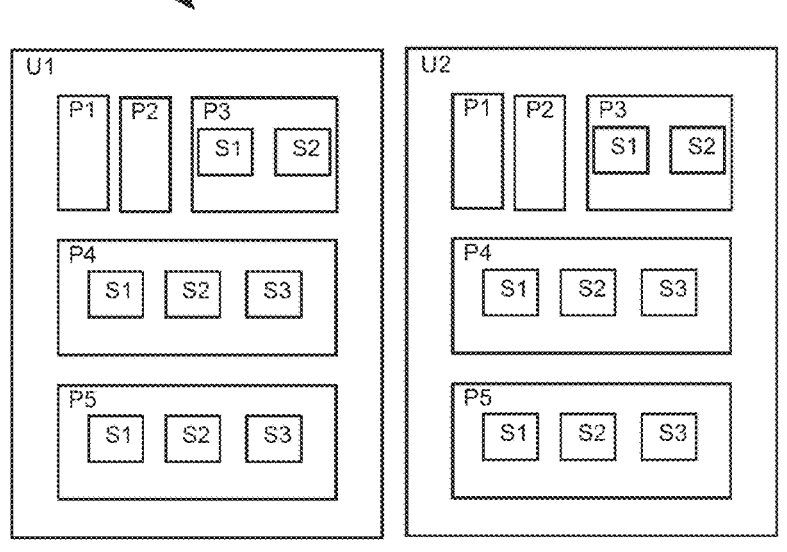
FIG. 3 illustrates a plurality of profiles, according to an embodiment described herein.
Figures 4A, 4B:
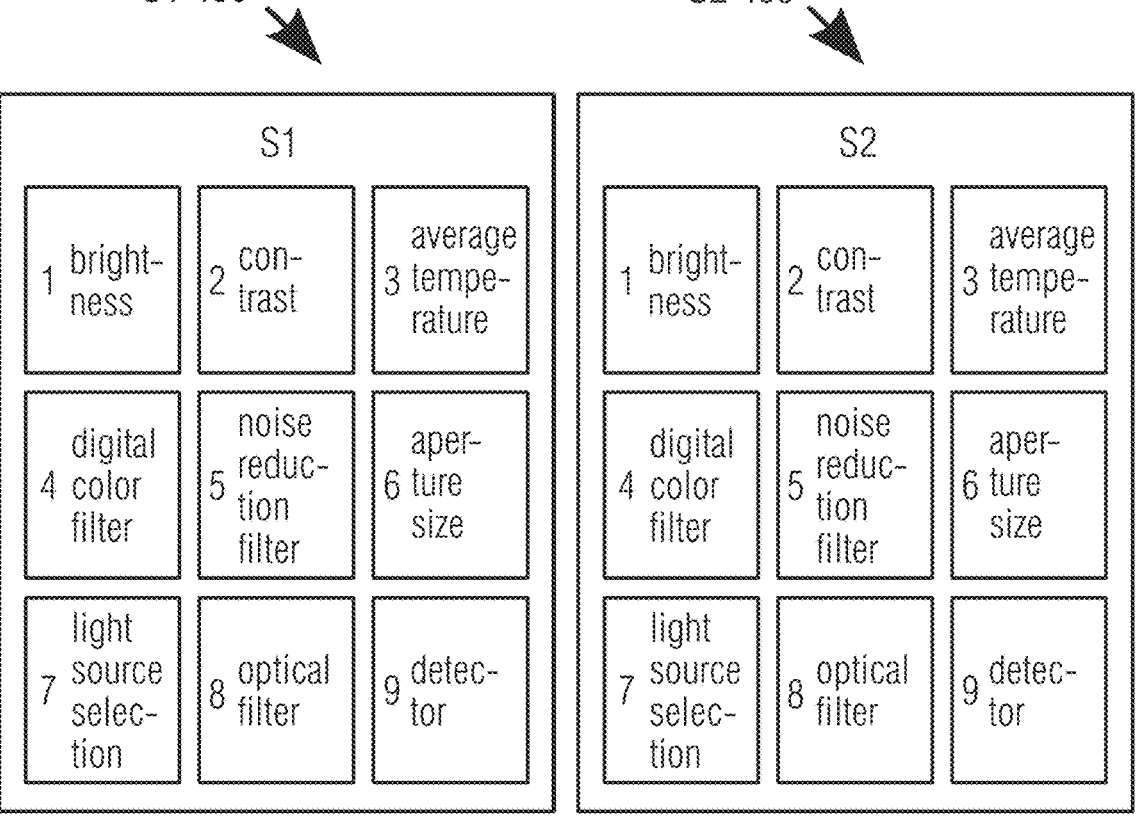
FIGS. 4A-4B illustrates settings, according to embodiments described herein.

FIG. 3 illustrates profiles 300. FIGS. 4A and 4B illustrate settings 400. Each profile 300 includes a plurality of settings 400. Settings 400 can include brightness 1, contrast 2, average temperature 3, a digital color filter 4 (which can have various forms, e.g. red filter, blue filter, green filter), noise reduction filter 5, an aperture size 6, light source selection 7, optical filter 8, detector 9, and any combinations thereof, for example. By application and/or selection of the settings 400, e.g. through the selection/determination of a profile 300, the image(s) 105 can be affected and/or determined. For example, when a profile 300 is determined 210, the settings 400 of the determine profile 300 are applied 220.

Profiles 300 can be stored in memory 107, e.g. in at least one memory. Profiles 300 can be accessed from a menu, selected by a user, and/or may be determined by an algorithm, for example. The settings 400 of a selected, determined, and/or applied profile 300 can be adapted to enhance or suppress anatomical features of an image(s) 105.

There can be multiple types of profiles 300. For example, there can be one or more user profiles U1, U2, which may include a default user profile U1. Each user profile U1, U2 can include a plurality of settings 400 (see FIGS. 4A and 4B). Other types of profiles are possible, such as procedure profiles P1, P2, P3, P4, P5 and/or scene profiles S1, S2, S3. The profiles 300 can be arranged in a hierarchy. Profiles 300 may include other profiles 300. The first scene profile S1 may be a subordinate profile to a procedure profile, e.g. P3S1 is the first scene profile of the third procedure profile.

For example, user profile(s) U1, U2 can be at the top of a hierarchy of profiles 300. Alternatively/additionally, scene profiles S1, S2, S3 may be at the bottom of the hierarchy. For example, a first scene profile S1 can include a plurality of settings S1-400 adapted to enhance or suppress anatomical features of a scene which the first scene profile S1 is adapted to enhance/suppress. A second scene profile S2 can include a plurality of settings S2-400 adapted to enhance or suppress anatomical features of a scene which the second scene profile S2 is adapted to enhance/suppress.

At least some of the profiles 300, such as each scene profile S1, S2, S3, can be configured to specifically enhance and/or suppress anatomical features of a respective image 105 and/or type of image. Feature enhancement/suppression can aid a medical practitioner in assessing an image of live tissue and/or of treating the tissue. Visualization of tissue structures can be highly important in surgical microscopy. There can be challenges with visualization approaches of traditional methods. There is a desire to streamline procedures and/or reduce error. Herein is disclosed means of providing reproducible and easy access to variable settings, such as digital and/or optical settings, which can aid a medical practitioner or user in assessing an image of live tissue.

The apparatus can receive a procedure selection (e.g. from a user). When received, the selection can determine the procedure profile P1, P2, P3. Alternatively/additionally, the apparatus can receive a scene selection, which, when received, can determine the scene profile S1, S2, S3.

Figure 5A:
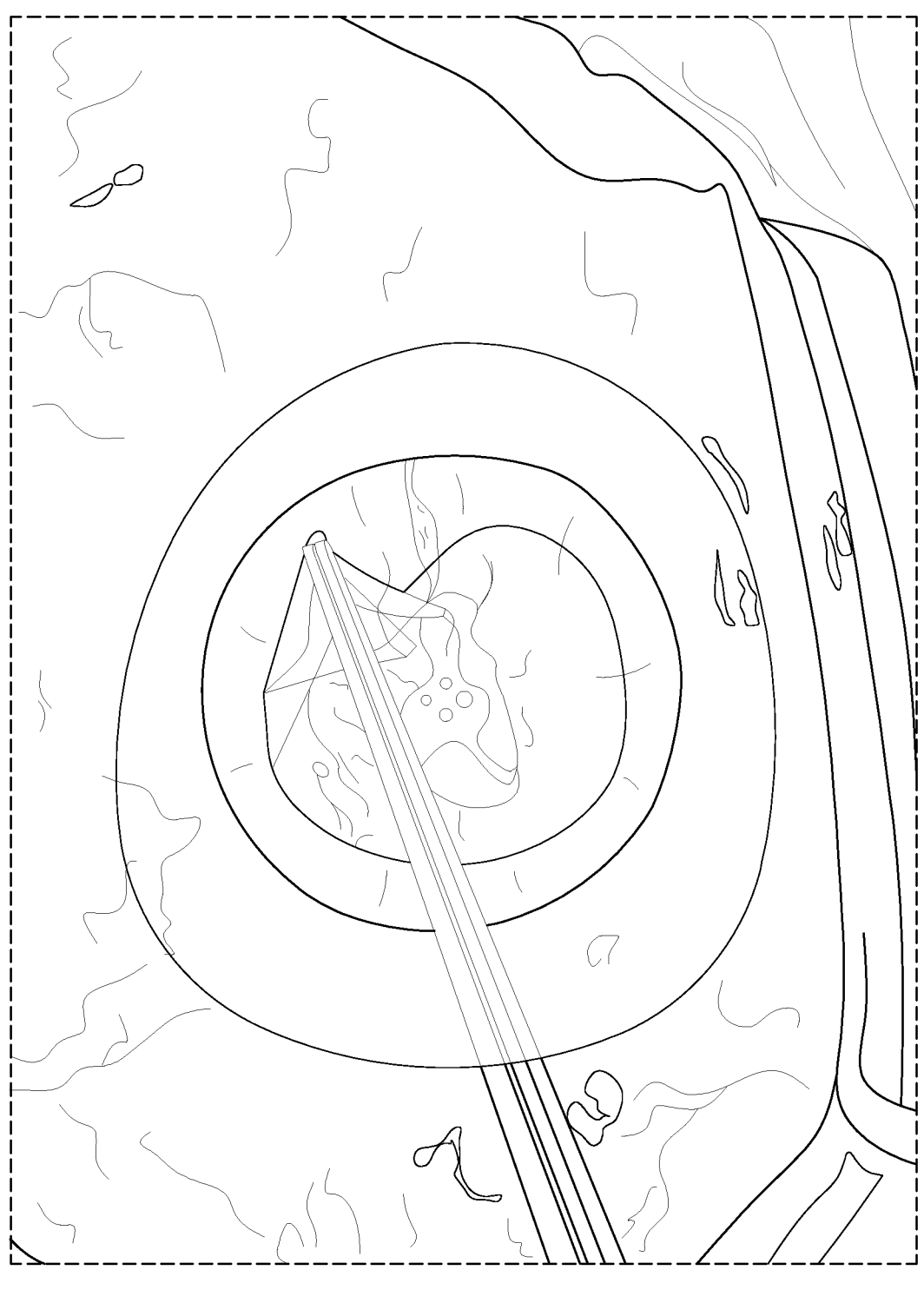
FIGS. 5A, 5B, and 5C each illustrates an image of living tissue.
Figure 5B:
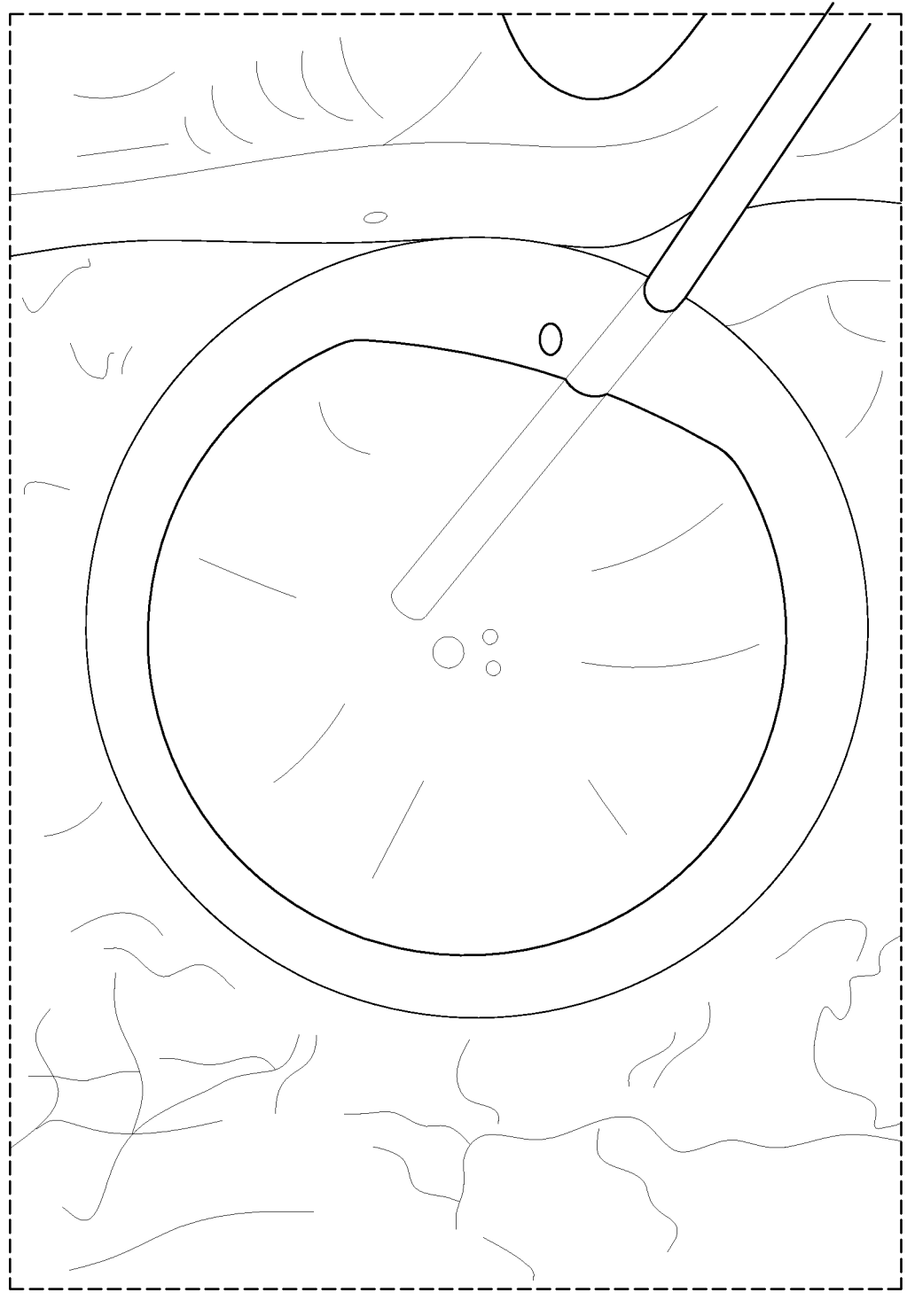

FIGS. 5A and 5B illustrate examples of images during cataract surgery. In FIG. 5A, the applied settings 400 are adapted to enhance the visualization of the posterior part of the capsule 550a. In the comparative example of FIG. 5B, the visualization of the posterior part of the capsule is poor, due to suboptimal settings 400 being applied. The applied settings 400 of FIG. 5A may be the settings of a first procedure profile P1 of a plurality of procedure profiles P1, P2, P3. The applied settings 400 of FIG. 5A may be designated the settings P1-400, e.g. the settings 400 determined by the first procedure profile P1. The first procedure profile P1, in this example, has exactly one plurality of settings P1-400 which are applied to determine the image 105. The first procedure profile P1 includes the settings P1-400 which are applied 220. The image 105, such as the appearance thereof, can be influenced/determined 240 by the applied settings P1-400.

In another example, the procedure profile P3 has two scene profiles S1, S2 (which can be written as P3S1 and P3S2 and groups of settings P3S1-400 and P3S1-400 associated with the scenes S1, S2 which are, in this example, subordinate to the procedure P3. (We note that S1, when subordinate to the third procedure P3, may include different settings P3S1-400 than when subordinate to the fourth procedure P4 which has settings P4S1-400 using this notation.)

Figure 5C:
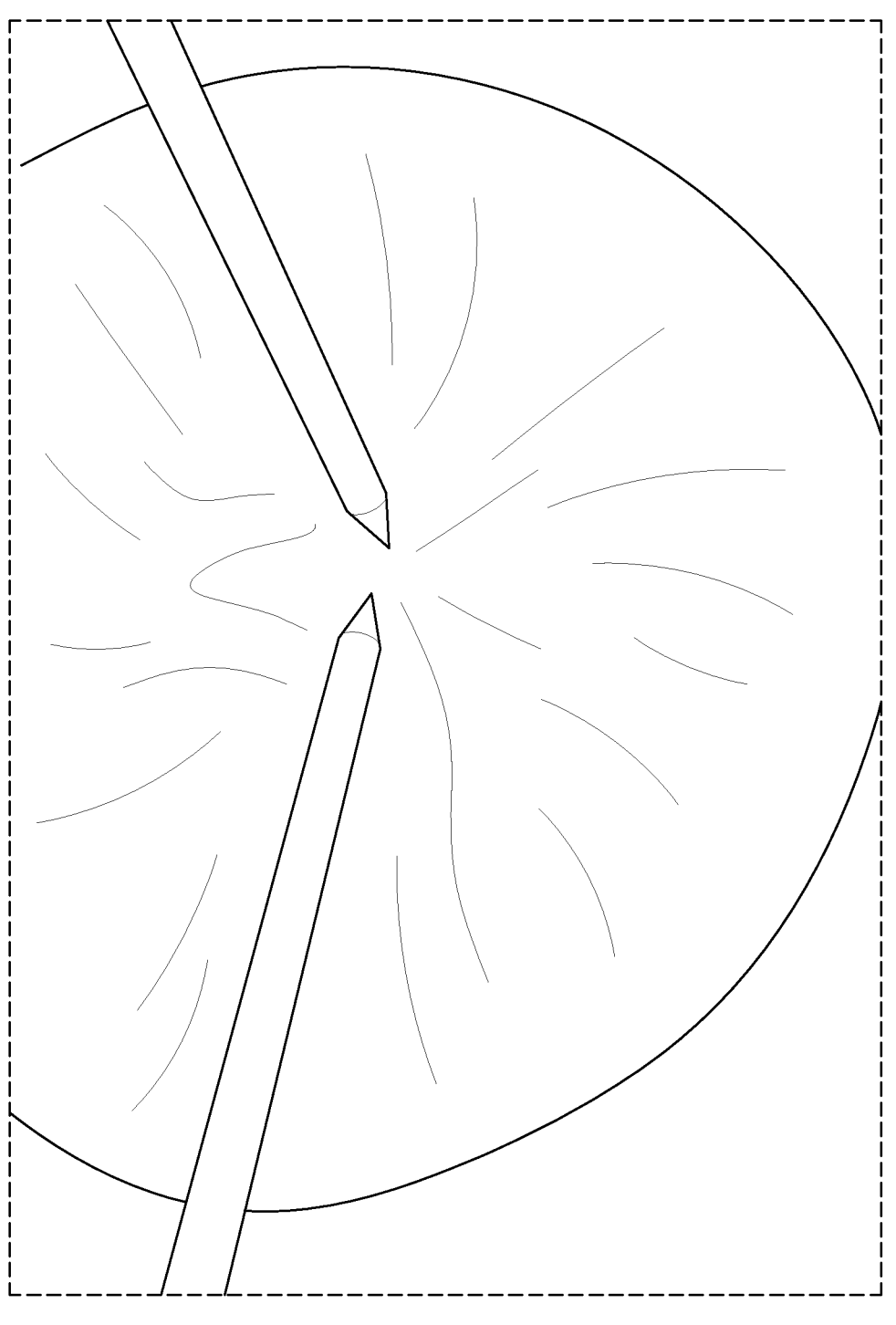

FIG. 5C illustrates a view of the posterior of the eye. The view of FIG. 5C illustrates again the challenges of imaging live tissue, including having optimal illumination. For example, tissue can be semi-translucent which can make it difficult to find settings 400 which allow for detailed imaging of anatomical features of interest. It can be desirable to have profiles 300 at hand which include settings 400 which can be rapidly applied, e.g. such that images can be generated which are optimal for tissue analysis and/or treatment.

FIG. 5D illustrates a view of the eye. The view of FIG. 5D illustrates again the challenges of imaging live tissue. For example, dyes can be used to stain features of live tissue, to aid in visualizing anatomical features. Settings 400 can be adjusted to optimize the contrast provided by the dye. Settings 400 from a profile 300 can be applied to enhance the contrast of a dye. More than one profile 300 for use in imaging dyed tissue can be stored in memory 107. There may be optimized settings 400 stored in multiple profiles 300, the profiles 300 for imaging different dyes each being configured to enhance the contrast of the different kinds of dyes. For example, a green enhancement profile 300 may enhance the contrast of a green dye. A blue enhancement profile 300 may enhance the contrast of a blue dye. In the image of FIG. 5D, a blue and/or green dye is used to enhance the epiretinal membrane during peeling.

Each procedure profile P1, P2, P3 may include settings 400, e.g. settings adapted for a particular procedure. For example, when a procedure can be performed entirely with one group of settings 400, the procedure profile P1 can, when determined and/or selected, determine the settings 400 used for the entire procedure. A procedure may have a predominant scene which may undergo only insignificant changes through the procedure. Returning to FIG. 3, procedure profiles P1 and P2 may each include respective settings P1-400 and P2-400, which are respectively applied 220 when the respective procedure profiles P1, P2 are determined/selected 210.

In another example, a profile 300 may be a procedure profile P3 which has multiple steps, such as a two-step procedure. A procedure profile P3, as illustrated in FIG. 3, can include multiple scene profiles, such as two scene profiles S1 and S2, which may be, in this case, subordinate to the procedure profile P3. The subordinate profiles may be designated P3S1 and P3S2, or, when user profile U1 is also part of the hierarchy, U1P3S1 and U1P3S2.

The first step of a two-step procedure may correspond to a first surgical scene. The first surgical scene may benefit from a first scene profile S1 which has a first group of settings S1-400 (see also FIG. 4). The second step of the procedure may correspond to a second surgical scene, and benefit from a second scene profile S2 which utilizes a second group of settings S2-400. In FIG. 3, many types of profiles 300 are represented, such as user profiles U1, U2, procedure profiles P1, P2, P3 . . . and scene profiles S1, S2, S3.

A procedure profile P1 that, for example, could be used to determine the image of FIG. 5A may be a red enhancement profile. A red enhancement profile may include an increased gain of the red channel, and/or may use long-pass filtered light. For example, the source and/or collection optics is filtered to pass red. Alternatively/additionally, a procedure profile may utilize a reduced aperture stop, such as to increase the depth of field; for example, the aperture may be decreased to pass ¼ or less, ⅛ or less, ¹⁄₁₆ or less, ¹⁄₃₂ or less, or ¹⁄₆₄ or less of the light as when fully opened. Smaller apertures may allow for increased depth of field.

For example, in cataract surgery, ophthalmologists can use the red reflex which can aid in visualizing the capsule, lens and anterior chamber structure of the eye. The red reflex can allow the viewing of the lens of the eye and/or the posterior capsule of the eye. The provided image can give information on the depth, such as the depth and position of instruments working within the eye. In dense cataracts, the penetration of light can be reduced by the opacity of the cataract lens, which can limit the view. The use of settings, such as the settings for red reflex can increase the utility of the image for the medical practitioner, e.g. by enhancing and/or suppressing anatomical features of the image. For example, longer wavelength light, e.g. red light, can be less susceptible to scatter, thus allowing for a more useful view of the eye, particularly in cataract surgery.

An apparatus may store settings 400 for cataract surgery within one or more profiles 300, e.g. within a procedure profile that may include subordinate profile(s).

A procedure profile P2 can be an example, e.g. a profile that utilizes red reflex settings, of one of a plurality of profiles 400 which can each be adapted to enhance and/or suppress anatomical features, according to the particular image or scene of interest, e.g. according to the anatomical features of interest of the surgical scene. In the examples of FIGS. 5A and 5B, the anatomical scene of the image 105 can be that of a cataract surgical procedure. The determined profile P2 can be a red reflex setting, for example, which applies a plurality of settings P2-400 to determine 240 the image 105 based on the applied settings P2-400.

For example, the determination 210 of the profile can include determining a procedure profile P1, P2, P3, P4, P5 from the plurality of profiles 300. Additionally, it is possible, at least for some determined procedure profiles P3, P4, P5, to further determine a scene profile S1 e.g. one of a plurality of scene profiles S1, S2, S3, from within a determined procedure profile P3, P4, P5. The applied settings 400 can be determined/selected from the determined scene profile S1, S2, S3. Herein, for example, a first scene profile S1 of a fourth procedure profile P4 of the first user profile U1 can be referred to as U1P4S1. The settings 400 thereof can be particularly referred to as U1P4S1-400.

For example, a surgical procedure may utilize a sequence of actions which may each benefit from particular settings. In such a case, it may be useful to have multiple profiles 300 (which include settings 400) accessible to the apparatus and/or medical practitioner. For example, a procedure can have two sub-procedures which each benefit from dissimilar settings 400, e.g. settings 400 which affect the relevant image(s) or scenes that are part of the procedure.

A procedure profile P3 can be determined which includes two scene profiles P3S1 and P3S2 (see FIG. 3). The scene profiles can each be configured to enhance/suppress respective anatomical features of respective images of the respective steps. The steps may be regarded as scenes of a multistep procedure. For example, a procedure profile P3 that is adapted for a procedure having exactly two steps can have two scene profiles S1, S2. Each of the scene profiles can have respective settings P3S1-400 and P3S2-400. For each step of the two-step procedure, scene profiles P3S1 and P3S2 can include the respective settings P3S1-400 and P3S2-400 which are applied 220 sequentially to determine each of two sequential images 105. A procedure profile, P3, P4, P5, can have one or more scene profiles S1, S2, S3 therein, for example.

In another example, a procedure profile, e.g. procedure profile P1 shown in FIG. 3, the procedures may have exactly one group of settings, P1-400 (e.g. one brightness setting, one contrast setting, one aperture setting, one gain setting, one set of filter settings). For example, a surgical procedure which can be performed without adjustment of the digital filter or optical settings may be able to utilize a single group of settings 400. In FIG. 3, procedure profiles P1 and P2 can each represent such settings for two different procedures, each of which can utilize a single group of settings P1-400, P2-400.

In FIG. 3, procedure profile P3 can represent a profile setting which has two groups of settings, e.g. two scene settings. Using the notation previously introduced, the determinable scene profiles of the procedure profile P3 can be represented as P3S1 and P3S2. Each of the profiles P3S1 and P3S2 have respective settings P3S1-400 and P3S1-400. A two-step procedure may benefit from an apparatus 100 which is configured with procedure profile P3. A medical professional may select the procedure profile P3; for each step of a two-step procedure for which procedure profile P3 is configured. The settings P3S1-400 and P3S1-400 of the procedure profile P3 can be applied, e.g. sequentially, in order to enhance/suppress the relevant anatomical features at each step of the surgical procedure.

The apparatus is not limited to use with two-step sequences. A procedure profile P1, P2, P3, P4, P5 may have any number of scene profiles S1, S2, S3 therein. FIG. 3 illustrates procedure profiles P4 and P5 which each have three scene profiles S1, S2, S3 therein. The determinable profiles 300 can result in the application 220 of settings 400 of each of the scene profiles P4S1, P4S2, P4S3 of a fourth procedure profile P4; and the application 220 of settings 400 of each of the scene profiles P5S1, P5S2, P5S3 of a fifth procedure profile P5, for example.

The apparatus 100 can be configured to output 250 image data sequentially, e.g. to output a plurality of sequential images at the respective pluralities of applied settings P3S1-400, P3S2-400 of each sequential scene profile P3S1, P3S2.

Outputting data 250 can include sequentially outputting a plurality of sequential images 105, each at respective applied settings S1-400, S2-400, S3-400 of each respective sequential scene profile S1, S2, S3. For example, when a 3-step procedure is performed, the apparatus can advance the settings with each step, and, at each step, image data can be determined 240 and output 250 which corresponds to images 105 at each step. It can be advantageous to have settings available in sequential fashion for a sequentially performed multistep surgical procedure, to allow for optimal visualization of features (or suppression of features, as the case may be) at each step of the procedure. Having settings 400 stored in memory 107, and accessible through profiles 300, may reduce error and allow efficient tissue analysis and treatment.

The apparatus may apply 220 the settings S2-400, S3-400 of a subsequent scene profile S2-400, S3-400, of a determined sequence of scene profiles S1, S2, S3. The apparatus can be configured for sequentially applying 220 the settings S1-400, S2-400, S3-400, including those of subsequent scene profiles S2, S3 of a determined sequence of scene profiles S1, S2, S3. For example, after applying the settings of S1-400, the settings of S2-400 are applied, then S3-400.

In an example, an advance command can be used to induce the apparatus to apply the settings of a subsequent scene profile S2, S3. For example, the apparatus receives an advance command, such as from a switch 106 (e.g. a footswitch) which causes the application of the settings S2-400 of a subsequent scene profile S2 (e.g. after setting S1-400).

Any of the settings 400 of any of the profiles 300 can possibly be modified. Modified settings can be stored in the at least one memory 107. Settings modifications can be based on user input.

The apparatus may have different user settings which may allow or forbid changing settings, e.g. depending on the permissions of the user. For example, basic users may be able to apply settings 400 and possibly modify settings (e.g. modify settings during use, such as to adjust the brightness of an image or light source). Basic users may be forbidden from storing modified settings in memory 107. For example, basic users may be forbidden from storing settings 400 after modification during use of the apparatus. Alternatively/additionally, modification of settings 400 associated with different profiles 300 that are accessible to other users may be forbidden.

The apparatus can determine a user profile from a plurality of user profiles. For example, a user may log-in such that the user profile is determined.

As indicated in FIG. 3, the profiles 300 may include user profiles U1, U2. For example, a first user profile U1 can be a default user profile U1. The default user profile U1 may have default settings 400 for each profile 300 therein (e.g. the procedure profiles U1P1, U1P2, U1P3, U1P4, U1P5 and/or scene profiles U1S1, U1S2, U1S3 which can be profiles 300 which are subordinate to the user profile U1). For example, the U1P1 profile has the default settings U1P1-400 for the first procedure profile P1.

A default profile, such as the first user profile U1 can include a plurality of default scene profiles U1P4S1, U1P4S2, U1P4S3, U1P5S1, U1P5S2, U1P5S3 of respective default procedure profiles U1P4, U1P5. The apparatus can include a default profile U1 which may include entirely default settings.

Permitted users may be able to store modified settings in memory 107. For example a permitted user can change and store settings associated with their own account, e.g. within the respective user profile. A second user U2, if permitted, may be able to modify and store settings 400 associated with at least some of the profiles 300 within the second user profile U2, e.g. U2P4S1, U2P4S2, U2P4S3, U2P5S1, U2P5S2, U2P5S3.

The apparatus can restore at least one of the settings to a default setting. For example, an inexperienced user may modify settings in an ineffective way and wish to return to a known setting. The default settings 400 of any profile 300 can be accessed to restore the settings. For example, each of the scene profiles S1, S2, S3 and/or procedure profiles P1, P2, P3, P4, P5 may have default settings stored in memory 107. The apparatus can restore at least one of the settings to a default setting, such as when a user selects a profile 300 for restoration of default settings.

In an embodiment, the apparatus can be configured to determine a sequence of sequential scene profiles P4S1, P4S2, P4S3; or P5S1, P5S2, P5S3, which can be determined from a determined procedure profile, e.g. P4 or P5. When applying 220 the plurality of settings 400, the sequential scene profiles P4S1, P4S2, P4S3; P5S1, P5S2, P5S3 are applied sequentially. The ability to sequentially apply settings 400 can aid a medical practitioner in reproducibly performing a multistep procedure while reducing errors attributable to suboptimal imaging conditions. Each of the settings 400 which are sequentially applied 220 can be adapted to enhance or suppress anatomical features of a relevant image 105, e.g. of one of a sequence of images.

Figure 6:
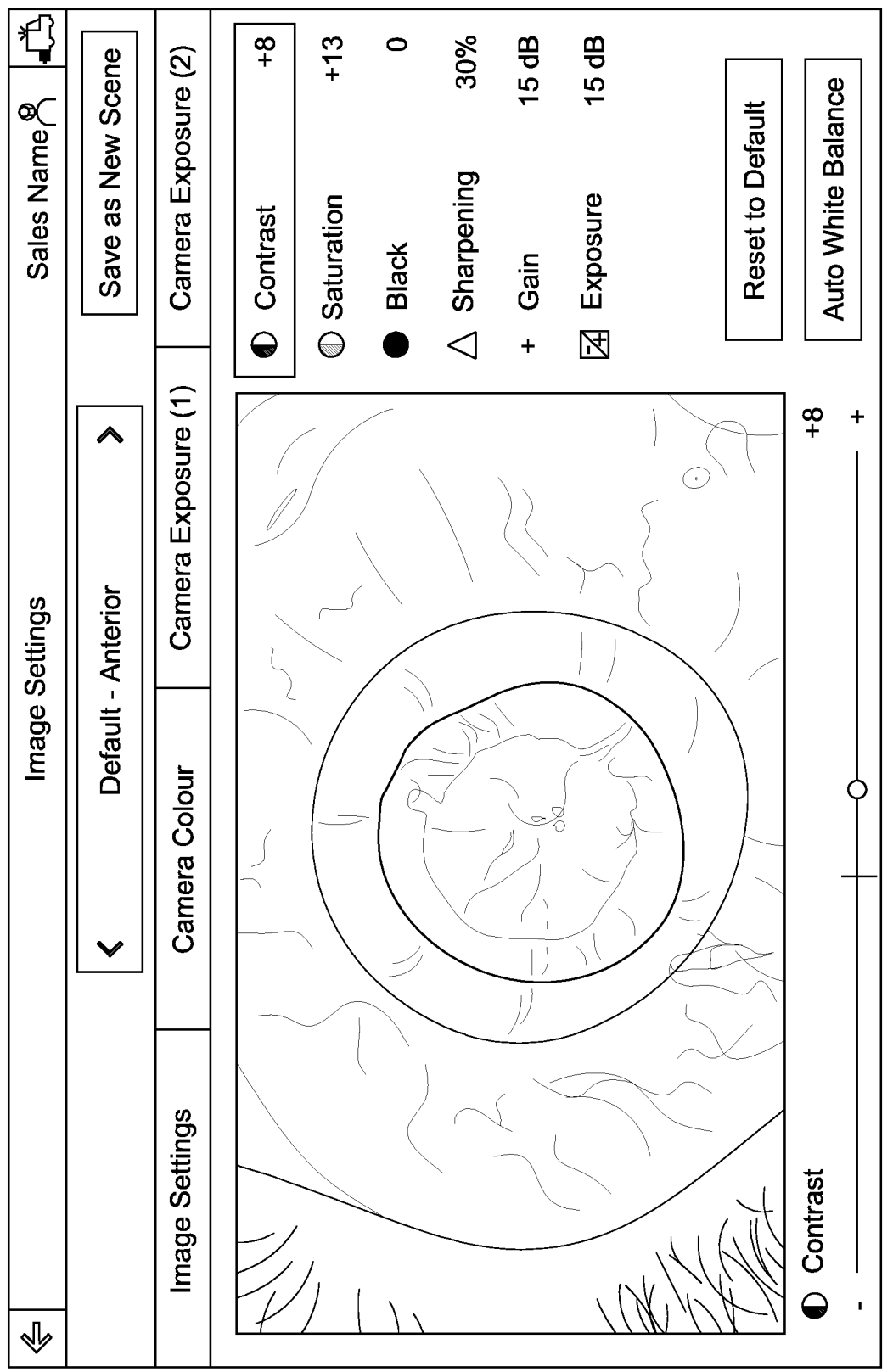
FIG. 6 illustrates an image of living tissue and settings.

FIG. 6 illustrates an image of living tissue and settings. FIG. 6 illustrates an example of settings used for enhancing ocular features. Settings can include contrast, saturation, black, sharpening, gain, and exposure. The applied settings can be from a determined/selected profile. The settings can be adjusted/modified with a graphical user interface (GUI). Optionally, a user may be able to save modified settings in a profile, such as a user profile, procedure profile, and/or scene profile. The GUI may include a menu which allows the determination/selection of different profiles. The selection/determination of a profile may result in the application of settings which change/determination the appearance of the image.

In an example, a scene profile can be set as the default setting of a procedure profile. For example, during cataract removal a scene profile adapted for the anterior scene of the eye can be applied. Subsequently, a scene profile adapted for the switch to the vitrectomy step in the posterior can be applied (e.g. first and second scene profiles P3S1 and P3S2 are sequentially applied during the procedure). The second scene profile P3S2 of the cataract removal profile P3 can be a vitreous filter, which can be automatically activated such as with the activation of a switch after completion of the first step.

A scene profile can be set as the default settings tied to a user profile U1, for example. A user could save their preferred scene profile S1 as a customized setting 400 in their profile U1, which may be automatically activated when they start their surgeries.

In an example, white balancing can be a setting 400. At least profile 300 can include adjusting the white balance, such as by taking into account the color temperature of a light source. For example, some users may prefer warmer tones (e.g. lower temperature), while others may prefer cooler tones (e.g. higher temperature). Some users may prefer the tones of a fluorescent light source and others may prefer halogen, while others the spectrum of LED lighting is preferable. The settings 400 may include setting color temperature, for example.

Figure 7:
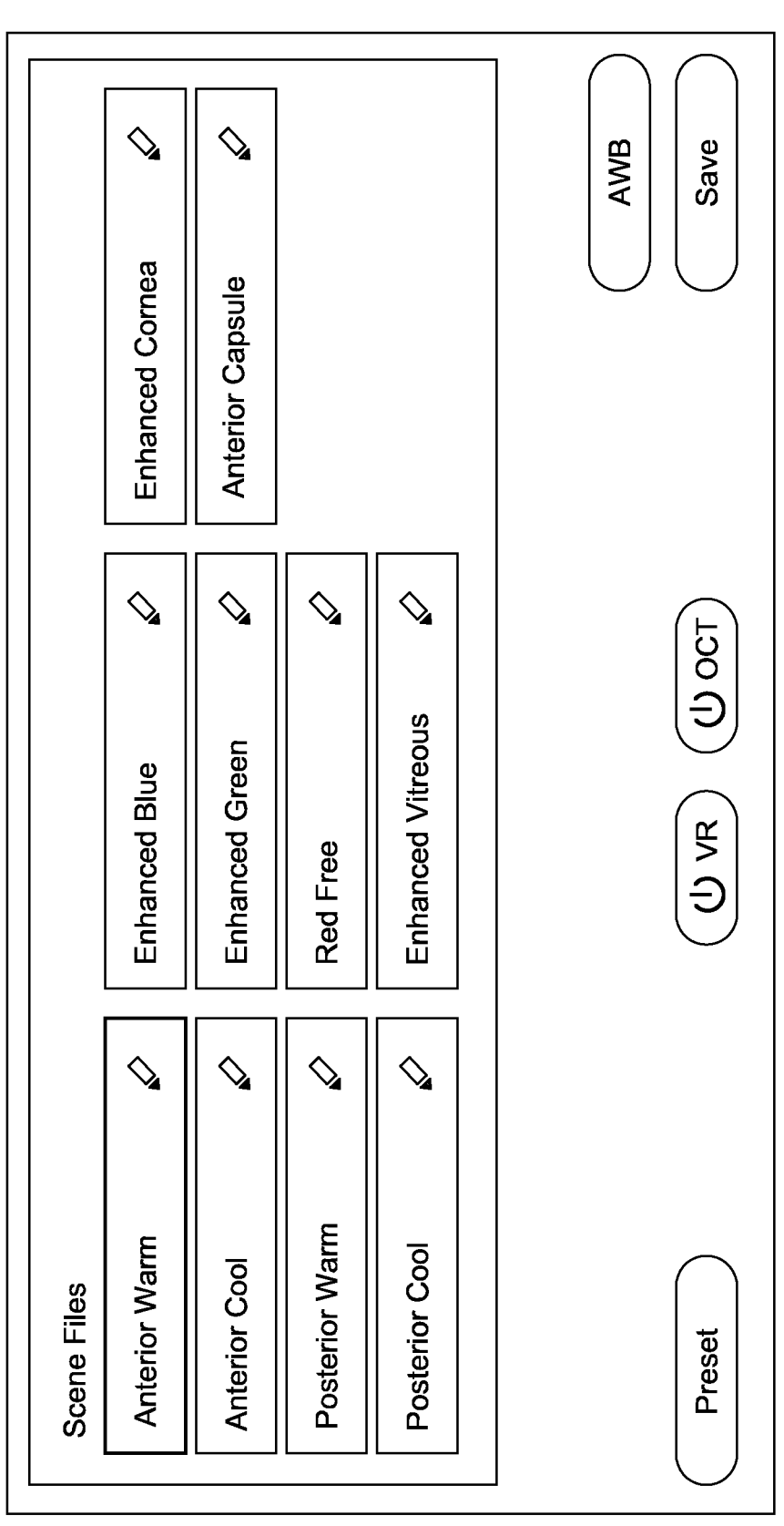
FIG. 7 illustrates a graphic user interface (GUI)

FIG. 7 illustrates a menu which can be used to read and/or adjust at least some settings 400, such as at least some of the settings 400 of a profile 300. Users can possibly make fine adjustment of the settings 400 of one or more profiles 300 (such as each profile, particularly if the permissions of the user allow it). Settings 400 can include contrast, shadows, highlights, saturation, brightness, aperture and color spectrum balance, which can be determined/modified to fit the requirements of the user's workflow and/or profile 300. A preset function on the interface can allow the changes to be reset back to original factory settings, e.g. default settings.

Figure 8:
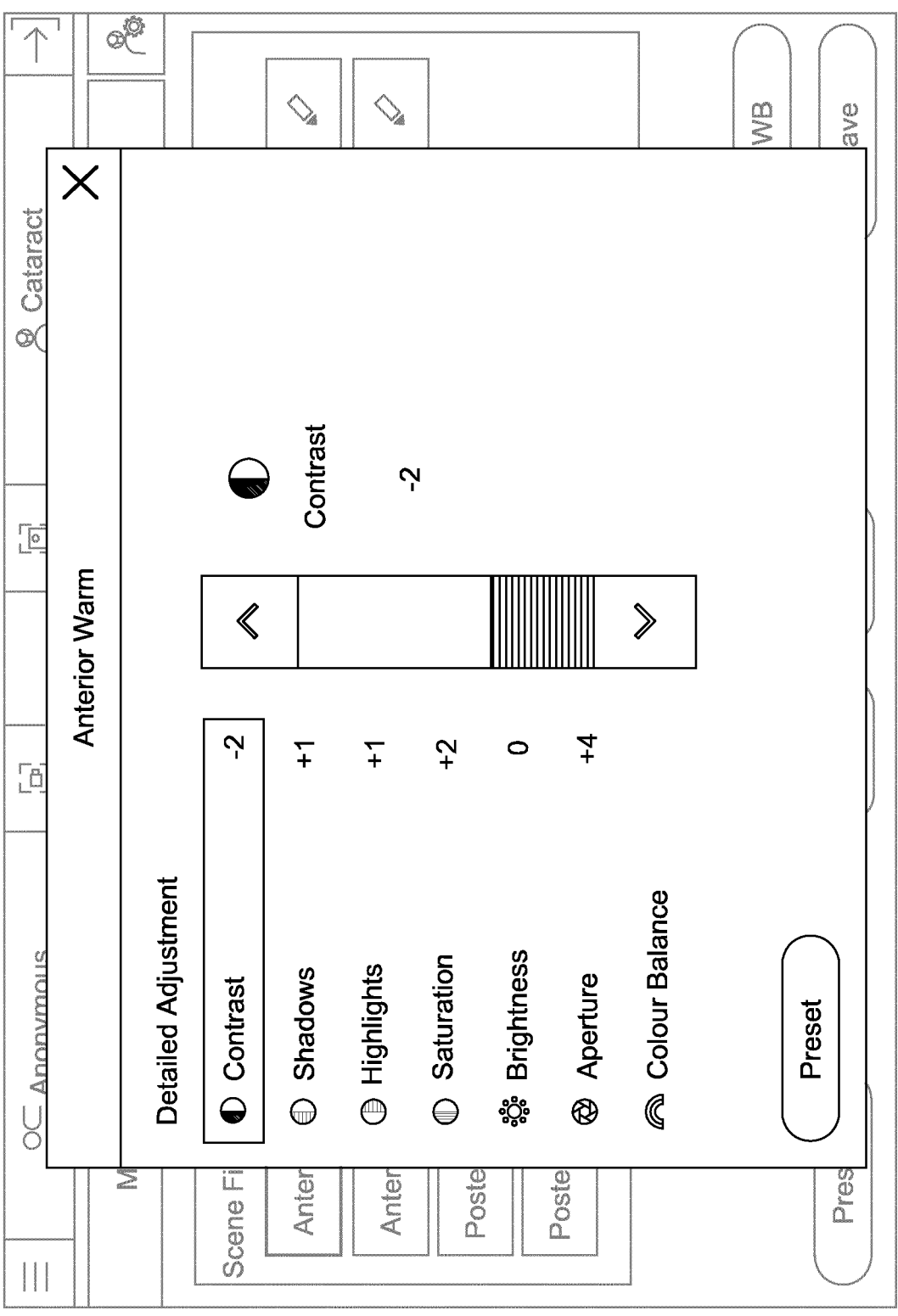
FIG. 8 illustrates a GUI.

FIG. 8 illustrates a menu. Settings 400 can be read and/or modified in the menu. The menu of FIG. 8 may illustrate at least some of the settings 400 included in a scene profile S1, S2, S3. For example, settings 400 can include contrast, shadows, highlights, saturation, brightness, aperture, and/or color balance. The menu of FIG. 8 can illustrate a scene profile S1, S2, S3 identified as "anterior warm" which can be adapted to show features of particular interest to a medical professional in the anterior of an eye, and at settings which are warm, (e.g. having a color temperature of about 2400-3000 K).

The following are examples of scene profiles:

reduced light profile and epiretinal membrane enhancement;

anterior profile and vitreous scene profile for anterior vitrectomy;

an epiretinal membrane enhancement profile comprising blue or green enhancement for enhancing the epiretinal membrane during peeling;

a vitreous scene profile comprising a blue filter or contrast adjustment for the visualisation of vitreous;

an anterior scene profile in which red reflex is enhanced and aperture is adjusted for increased depth of field;

a reduced light profile comprising an increased camera exposure time and noise reduction for improving low illumination visualization in the posterior of the eye;

a red enhancement profile comprising an increase in gain of a red channel, for highlighting the posterior capsule for lowering the risk of posterior capsule rupture;

a red-free filter profile for identifying an area for placing a port during hemorrhage;

a red-free filter profile for identifying the retina;

an orange/reddish enhancement profile for aiding differentiation of cornea layers during stripping of a cornea endothelial or descemet's membrane;

a dense cataract profile for adjustment of contrast and enhancing blue or green dye used during rhexis and phacoemulsification of dense cataract lens;

a temperature profile for at least one of: a cool setting, a warm setting, a 3000 K setting, 4000 K setting, 5000 K setting, a halogen lamp appearance, a fluorescent light appearance, or white LED appearance; and a dye enhancement profile for enhancing contrast from dyes such as indocyanine green, fluorescein, or trypan blue.

The apparatus can be configured to hold in memory at least one of the above described scene profiles. Yet further scene profiles can be generated by combining more than one of the above described scene profiles, when the constituent scene profiles have settings that are not inconsistent with each other. Such combination scene profiles can also be stored in the at least one memory 107. For example, a scene file profile can include a reduced light profile in combination with epiretinal membrane enhancement. In another example, the anterior profile can be combined with the vitreous scene profile, such as for an anterior vitrectomy procedure.

The following are examples of procedure profiles:

a cataract procedure profile, comprising: a temperature profile, a red enhancement profile, and a vitreous scene profile for anterior vitrectomy;

a retinal procedure profile, comprising: a temperature profile, an epiretinal membrane enhancement profile, a vitreous scene profile, a reduced light profile, a red-free filter profile, and a dye enhancement profile;

a corneal procedure profile, comprising: a temperature profile, an orange/reddish enhancement profile for aiding differentiation of cornea layers, and a red enhancement profile; and a macular pucker profile, comprising: a temperature profile, an epiretinal membrane enhancement profile, a vitreous scene profile, a reduced light profile, a red-free filter profile, and a dye enhancement profile.

The apparatus can be configured to hold in memory at least one of the above described procedure profiles.

Herein, an aperture adjustment for increased depth of field can utilize a reduced aperture stop; for example, the aperture may be decreased to pass $\frac{1}{4}$ or less, $\frac{1}{8}$ or less, $\frac{1}{16}$ or less, $\frac{1}{32}$ or less, or $\frac{1}{64}$ or less of the light as when fully opened. Smaller apertures may allow for increased depth of field.

Herein GUI and menu may be used interchangeably.

Herein, in an embodiment which can be combined with any other embodiment, a plurality of procedure profiles can include at least one procedure profile which includes a plurality of scene profiles.

Herein, in an embodiment which can be combined with any other embodiment, a plurality of procedure profiles can include at least one procedure profile which includes exactly one group of settings. The exactly one group of settings can be applied when the procedure profile is determined.

Herein, in an embodiment which can be combined with any other embodiment, each scene profile can include exactly one respective group of settings which are each applied, respectively, when the respective scene profile is determined/selected.

Herein, in an embodiment which can be combined with any other embodiment, an advance command can induce the end of the application of settings of a previously applied scene profile, and induce the application of the settings of a subsequent scene profile.

Herein, in an embodiment which can be combined with any other embodiment, a subsequent scene profile can be configured to be applied after a previous scene profile.

Returning to FIG. 1, a schematic illustration of a surgical microscope 100 is shown which is configured to perform a method described herein. The surgical microscope 100, which can be an ophthalmic microscope, comprises an imaging device 104 and the apparatus 102 as described herein, which may be a computer system. The imaging device 104 is configured to take images and is connected to the apparatus 102. The apparatus 102 is configured to execute at least a part of a method described herein. The apparatus 102 may be configured to execute a machine learning algorithm. The apparatus 102 and imaging device 104 may be separate entities but can also be integrated together in one common housing. The apparatus 102 may be part of a central processing system of the imaging device 104 and/or the apparatus 102 may be part of a subcomponent of the imaging device 104, such as a sensor, an actor, a camera or an illumination unit, etc. of the imaging device 104.

The apparatus 102 may be a local computer device (e.g. personal computer, laptop, tablet computer or mobile phone) with one or more processors and one or more storage apparatuses or may be a distributed computer system (e.g. a cloud computing system with one or more processors and one or more storage apparatuses distributed at various locations, for example, at a local client and/or one or more remote server farms and/or data centers). The apparatus 102 may comprise any circuit or combination of circuits.

The apparatus 102 may include a communications system, such as a removable communications system.

In one embodiment, the apparatus 102 may include one or more processors which can be of any type. As used herein, processor may mean any type of computational circuit, such as but not limited to a microprocessor, a microcontroller, a complex instruction set computing (CISC) microprocessor, a reduced instruction set computing (RISC) microprocessor, a very long instruction word (VLIW) microprocessor, a graphics processor, a digital signal processor (DSP), multiple core processor, a field programmable gate array (FPGA), for example, of a microscope or a microscope component (e.g. camera) or any other type of processor or processing circuit. Other types of circuits that may be included in the apparatus 102 may be a custom circuit, an application-specific integrated circuit (ASIC), or the like, such as, for example, one or more circuits (such as a communication circuit) for use in wireless apparatuses like mobile telephones, tablet computers, laptop computers, two-way radios, and similar electronic systems. The apparatus 102 may include one or more storage apparatuses, which may include one or more memory elements suitable to the particular application, such as a main memory in the form of random access memory (RAM), one or more hard drives, and/or one or more drives that handle removable media such as compact disks (CD), flash memory cards, digital video disk (DVD), and the like. The apparatus 102 may also include a display device, one or more speakers, and a keyboard and/or controller, which can include a mouse, trackball, touch screen, voice-recognition device, or any other device that permits a system user to input information into and receive information from the apparatus 102.

Some or all of the method steps may be executed by (or using) a hardware apparatus, like for example, a processor, a microprocessor, a programmable computer or an electronic circuit. In some embodiments, some one or more of the most important method steps may be executed by such an apparatus.

Depending on certain implementation requirements, embodiments of the invention can be implemented in hardware or in software. The implementation can be performed using a non-transitory storage medium such as a digital storage medium, for example a floppy disc, a DVD, a Blu-Ray, a CD, a ROM, a PROM, and EPROM, an EEPROM or a FLASH memory, having electronically readable control signals stored thereon, which cooperate (or are capable of cooperating) with a programmable computer system such that the respective method is performed. Therefore, the digital storage medium may be computer readable.

Some embodiments according to the invention comprise a data carrier having electronically readable control signals, which are capable of cooperating with a programmable computer system, such that one of the methods described herein is performed.

Generally, embodiments of the present invention can be implemented as a computer program product with a program code, the program code being operative for performing one of the methods when the computer program product runs on a computer. The program code may, for example, be stored on a machine readable carrier.

Other embodiments comprise the computer program for performing one of the methods described herein, stored on a machine readable carrier.

In other words, an embodiment of the present invention is, therefore, a computer program having a program code for performing one of the methods described herein, when the computer program runs on a computer.

A further embodiment of the present invention is, therefore, a storage medium (or a data carrier, or a computer-readable medium) comprising, stored thereon, the computer program for performing one of the methods described herein when it is performed by a processor. The data carrier, the digital storage medium or the recorded medium are typically tangible and/or non-transitionary. A further embodiment of the present invention is an apparatus as described herein comprising a processor and the storage medium.

A further embodiment of the invention is, therefore, a data stream or a sequence of signals representing the computer program for performing one of the methods described herein. The data stream or the sequence of signals may, for example, be configured to be transferred via a data communication connection, for example, via the internet.

A further embodiment comprises a processing means, for example, a computer or a programmable logic device, configured to, or adapted to, perform one of the methods described herein.

A further embodiment comprises a computer having installed thereon the computer program for performing one of the methods described herein.

A further embodiment according to the invention comprises an apparatus or a system configured to transfer (for example, electronically or optically) a computer program for performing one of the methods described herein to a receiver. The receiver may, for example, be a computer, a mobile device, a memory device or the like. The apparatus or system may, for example, comprise a file server for transferring the computer program to the receiver.

In some embodiments, a programmable logic device (for example, a field programmable gate array) may be used to perform some or all of the functionalities of the methods described herein. In some embodiments, a field programmable gate array may cooperate with a microprocessor in order to perform one of the methods described herein. Generally, the methods are preferably performed by any hardware apparatus.

| List of reference signs | |
| --- | --- |
| apparatus | 102 |
| processor(s) | 101 |
| image | 105 |
| display | 111 |
| memory | 107 |
| surgical microscope | 100 |
| switch | 106 |
| imaging device | 104 |
| method | 200 |
| determining a profile | 210 |
| applying settings | 220 |
| determining an image | 240 |
| outputting | 250 |
| profiles | 300 |
| user profiles | U1, U2 |
| procedure profiles | P1, P2, P3, P4, P5 |
| scene profiles | S1, S2, S3 |
| settings | 400 |
| settings | 1-9 |
| settings | S1-400, S2-400 |

The invention claimed is:

1. An apparatus for determining image data of tissue, comprising:
at least one processor, wherein
the apparatus is configured for:
determining a procedure profile from a plurality of procedure profiles, wherein each procedure profile includes settings for a particular surgical procedure;
determining a scene profile from the determined procedure profile, wherein each procedure profile includes one or more scene profiles, the determined scene profile is a sub-ordinate profile of the determined procedure profile, and each scene profile includes image processing settings for a particular scene of a particular surgical procedure to enhance or suppress anatomical features;
applying a plurality of settings from the determined scene profile;
determining at least one image based on the applied settings; and
outputting data for displaying the at least one image.

2. The apparatus of claim 1, further comprising:
at least one memory configured for storing the plurality of profiles and the plurality of settings.

3. The apparatus of claim 1, wherein the apparatus is configured for:
determining a sequence of sequential scene profiles from the determined procedure profile.

4. The apparatus of claim 3, wherein the apparatus is configured such that:
applying the plurality of settings includes sequentially applying the sequential scene profiles.

5. The apparatus of any of claim 3, wherein the apparatus is configured such that:
outputting data includes sequentially outputting a plurality of sequential images at the respective pluralities of applied settings of each sequential scene profile.

6. The apparatus of claim 3, wherein the apparatus is configured for applying the settings of a subsequent scene profile of the determined sequence of scene profiles.

7. The apparatus of claim 6, wherein the apparatus is configured for receiving an advance command, and, when the advance command is received, applying the settings of the subsequent scene profile.

8. The apparatus of claim 6, further comprising:
a switch for transmitting the advance command for advancing to the settings of the subsequent scene profile.

9. The apparatus of claim 1, wherein the apparatus is configured such that applying the plurality of settings from the determined profile includes at least one of:
processing the image data, or
transmitting a control signal to adjust an optical setting.

10. The apparatus of claim 1, wherein the apparatus is configured such that:
the scene profiles include at least one of the following:
an epiretinal membrane enhancement profile comprising blue or green enhancement for enhancing the epiretinal membrane during peeling;
a vitreous scene profile comprising a blue filter or contrast adjustment for the visualisation of vitreous;
an anterior scene profile in which red reflection is enhanced and an aperture is reduced to increase the depth of field;
a reduced light profile comprising an increased camera exposure time and noise reduction for improving low illumination visualization in the posterior of the eye;
a red enhancement profile comprising an increase in gain of a red channel, for highlighting the posterior capsule for lowering the risk of posterior capsule rupture;
a red-free filter profile for identifying an area for placing a port during hemorrhage;
a red-free filter profile for identifying the retina;
an orange-reddish enhancement profile for aiding differentiation of cornea layers during stripping of a cornea endothelial or descemet's membrane;
a dense cataract profile for adjustment of contrast and enhancing blue or green dye used during rhexis and phacoemulsification of dense cataract lens;
at least one temperature profile for at least one of: a cooler setting, a warmer setting, a 3000 K setting, 4000 K setting, 5000 K setting, a halogen lamp appearance, a fluorescent light appearance, or white LED appearance; or
a dye enhancement profile for enhancing contrast from dyes such as indocyanine green, fluorescein, or trypan blue.

11. The apparatus of claim 1, wherein the apparatus is configured such that:
the plurality of procedure profiles includes at least one of the following:
a cataract procedure profile, comprising at least two of: a temperature profile, a red enhancement profile, or a vitreous scene profile for anterior vitrectomy;
a retinal procedure profile, comprising at least two of: a temperature profile, an epiretinal membrane enhancement profile, a vitreous scene profile, a reduced light profile, a red-free filter profile, or a dye enhancement profile;
a corneal procedure profile, comprising at least two of: a temperature profile, an orange-reddish enhancement profile for aiding differentiation of cornea layers, or a red enhancement profile; or
a macular pucker profile, comprising at least two of: a temperature profile, an epiretinal membrane enhancement profile, vitreous scene profile, a reduced light profile, red-free filter profile, or a dye enhancement profile.

12. The apparatus of claim 1, wherein the apparatus is configured for:

restoring at least one of the settings to a default setting, wherein a plurality of default settings is stored in the at least one memory.

13. A surgical microscope comprising the apparatus of claim 1.

14. A method of determining at least one image, comprising:

determining a procedure profile from a plurality of procedure profiles, wherein each procedure profile includes settings for a particular surgical procedure;

determining a scene profile from the determined procedure profile, wherein each procedure profile includes one or more scene profiles, the determined scene profile is a sub-ordinate profile of the determined procedure profile, and each scene profile includes image processing settings for a particular scene of a particular surgical procedure to enhance or suppress anatomical features;

applying a plurality of settings from the determined scene profile;

determining the at least one image based on the applied settings; and outputting data for displaying the at least one image.

15. A non-transitory, computer-readable medium comprising a program code that, when the program code is executed on a processor, a computer, or a programmable hardware component, causes the processor, computer, or programmable hardware component to perform the method of claim 14.

\* \* \* \* \*